United States Patent [19]
Duthie et al.

[11] Patent Number: 5,876,934
[45] Date of Patent: Mar. 2, 1999

[54] DNA SEQUENCING METHOD

[75] Inventors: Scott Duthie, Milwaukee, Wis.; Pierre Sevigny, Montreal, Canada; Tomas Hultman, Upplandväfby, Sweden; Hartmut Voss, Leimen, Germany

[73] Assignee: Pharmacia Biotech Inc., Milwaukee, Wis.

[21] Appl. No.: 768,550

[22] Filed: Dec. 18, 1996

[51] Int. Cl.⁶ .............................. C12Q 1/68; C12P 19/34
[52] U.S. Cl. ................................................ 435/6; 435/91.2
[58] Field of Search ........................................ 435/6, 91.2

[56] References Cited

U.S. PATENT DOCUMENTS 5,436,149  7/1995  Barnes ..................................... 435/194

FOREIGN PATENT DOCUMENTS 0 516 245 A1  12/1992  European Pat. Off. .
0 629 706 A2  12/1994  European Pat. Off. .
WO 90/03443   4/1990   WIPO .

OTHER PUBLICATIONS

P.J. Barr, et al., "7–deaza–2'–deoxyguanosine–5'–triphosphate: Enhanced resolution in M13 dideoxy sequencing," *BioTechniques* 4(5) :428–432, 1986.

M.A. Innis, et al., "DNA sequencing with *Thermus aquaticus* DNA polymerase and direct sequencing of polymerase chain reaction–amplified DNA," *Proc. Natl. Acad. Sci. USA* 85:9436–9440, 1988.

D.R. Mills and F.R. Kramer, "Structure–independent nucleotide sequence analysis," *Proc. Natl. Acad. Sci. USA* 76 (5) :2232–2235, 1979.

S. Tabor and C.C. Richardson, "DNA sequence analysis with a modified bacteriophage T7 DNA polymerase," *Proc. Natl. Acad. Sci. USA* 84 (14) :7467–4771, 1987.

H. Dierick, et al., "Incorporation of dITP or 7–deaza dGTP during PCR improves sequencing of the product," *Nucl. Acids Res.* 21 (18) :4427–4428, 1993.

Kambara et al (Biotechnology vol. 9) pp. 648–651, 1991.

Ansorge et al J. Biochem. Biophy. Meth. vol. 20 pp. 47–52, 1989.

*Primary Examiner*—Eggerton A. Campbell
*Attorney, Agent, or Firm*—Quarles & Brady

[57] ABSTRACT

A method of sequencing a DNA molecule is disclosed. This method comprises the step of exposing the molecule to a mixture of dITP/dGTP in a sequencing elongation reaction whereby compression artifacts are reduced.

12 Claims, 11 Drawing Sheets

DNA SEQUENCING METHOD

BACKGROUND OF THE INVENTION

The development of dependable methods for sequence analysis of DNA (deoxyribonucleic acid) has lead to the success of recombinant DNA methodologies and the field of genetic engineering. DNA sequencing is generally accomplished by the method of Sanger, et al. (*Proc. Natl. Acad. Sci. USA* 74:5463–5467, 1977) and involves the in vitro enzymatic synthesis of single-stranded DNA starting from either a single- or double-stranded DNA template. In the original embodiment of the protocol, a primer, usually a synthetic oligonucleotide 15 to 30 bases in length, is first annealed to its complementary sequence on the template of the single-stranded DNA to be sequenced. The 3'-end of this primer is extended by the Klenow fragment of *E. coli* DNA polymerase I in the presence of 2'-deoxynucleoside 5'-triphosphates (dNTPs), one of which contains a radiolabel.

Four separate sequencing reactions are performed, each buffered reaction containing all four dNTPs (2'-deoxyadenosine 5'-triphosphate (dATP), 2'-deoxycytidine 5'-triphosphate (dCTP), 2'-deoxyguanosine 5'-triphosphate (dGTP), and 2'-deoxythymidine 5'-triphosphate (dTTP), and a small amount of one specific 2', 3'-dideoxynucleoside 5'-triphosphate chain-terminating agent (either ddATP, ddCTP, ddGTP, or ddTTP; or, in general, ddNTP).

By varying the ratio of the specific chain-terminating ddNTP to its dNTP analog in a particular reaction, the polymerase generates a population of fragments where a specific ddNTP is substituted at every possible position along the DNA template where the corresponding dNTP would have been incorporated. Once the one-step labelling and termination step has been completed, an excess of all four dNTPs are added to each reaction to "chase" all fragments not terminated by a specific ddNTP into higher molecular weight DNA.

The products of the four separate reactions are then fractionated and visualized in adjacent lanes on a high resolution denaturing polyacrylamide gel system.

In 1987 Tabor and Richardson (Tabor, S. and C. C. Richardson, *Proc. Natl. Acad. Sci. USA* 84:4767–4771, 1987) described a modification of the basic Sanger protocol for use with T7 DNA polymerase which separated the labelling from the termination step, or a two-step sequencing protocol. T7 DNA polymerase and a limiting amount of all four dNTPs, one of which was radiolabeled, were added to an annealed template and primer. During a short incubation step at a suboptimal polymerization temperature (e.g., room temperature) the polymerase added one to several hundred dNTPs to the 3'-end of the primer, while also incorporating the radiolabeled dNTP in all of the extended fragments. At the end of the labelling step, the mixture was allocated equally into four separate termination reactions. Each termination reaction contained nonlimiting concentrations of all four dNTPs and one specific ddNTP.

Following a second short incubation step at the optimal polymerization temperature for the DNA polymerase (DNAP) (e.g., 37° C.), detection of the DNA fragments was as outlined for the Sanger protocol. The final process in both of the radiolabeled sequencing protocols described above included reading the autoradiogram to generate an ordered DNA sequence and then manual entry of this sequence into a data base for subsequent manipulations.

In 1989 Murray (Murray, V., *Nucl. Acids Res.* 17:8889, 1989) described a novel method for sequence generation from DNA templates using ddNTP termination of the DNA fragments. Murray applied a variation of the polymerase chain reaction (Mullis, K. B., et al., *Cold Spring Harbor Symp. Quant. Biol.* 51:263–273, 1986; Saike, R. K., et al., *Science* 230:1350–1354, 1985) which has become known as "cycle sequencing". Cycle sequencing has the advantage of using smaller amounts of template DNA than those sequencing methods described previously.

Since the mid-1980's commercially available DNA sequencing instruments have automated the gel electrophoresis, data collection, sequence generation and data entry steps involved with the radiolabeled methods described above. In addition, particular automated instruments have taken advantage of certain dyes that emit photon energy when excited with a laser, eliminating the need to use radioactivity to detect the separated DNA fragments. All of the instruments incorporate a high resolution polyacrylamide gel system for separation of the labelled DNA fragments. Each instrument also contains some form of detection system at a fixed point across the length of the gel near its bottom to detect the fluorescent-labelled fragments as they migrate during electrophoresis.

There are at present commercially available automated instruments based upon the detection technologies of: (1) single fluorescent-labelled primers or dNTPs with the sequencing reactions run and detected in separate lanes of a gel (Ansorge, W., et al., *Nucl. Acids Res.* 15:4593–4602, 1987), (2) primers labelled with four separate fluors (Smith, L., et al., *Nucl. Acids Res.* 13:2399–2412, 1985; Smith, L., et al., *Nature* 321:674–679, 1986) allowing all four reactions to be run and detected in one lane on a gel, or (3) the same strategy as in (2), above, except with the substitution of four different fluorescent-labelled ddNTPs for the labelled primers (Prober, J., et al., *Science* 238:336–341, 1987).

One problem encountered by all sequencing methodologies is sequence compression caused by DNA secondary structure during electrophoresis. The relatively short DNA fragments produced in the sequencing reaction fold back upon themselves, forming tight interstrand loops and hairpin turns. Some of these structures have sufficient strength that they are not completely denatured by heating or electrophoresis through 7–8M urea. The incompletely denatured fragments, which may result from either A:T or G:C base pairs, migrate faster through the gel matrix than surrounding fragments of similar length, causing fragments that should differ by one to a few nucleotides to comigrate and appear as overlapping peaks (see FIG. 1, arrow). Unambiguous sequence determination is impossible in areas where compression artifacts occur. One typical way to resolve the sequence in an area of a compression is to sequence the opposite DNA strand (Davies, R. W., *Gel Electrophoresis of Nucleic Acids, A Practical Approach* IRL Press, pp. 148–149, 1985).

Due to the cost involved with opposite strand sequencing various other strategies have evolved to combat compressions. These alternate strategies include running the sequencing gels at elevated temperatures and/or substituting modified dNTPs into the sequencing mixes. Two of these modified dNTPs usually are dATP and dGTP where the nitrogen molecule at position 7 on the base moiety has been changed to a carbon atom ($c^7$dATP and $c^7$dGTP, respectively). Both $c^7$dATP and $c^7$dGTP decrease by one the number of hydrogen bonds formed during base pairing of these molecules with their respective dNTP counterparts. The overall effect is to lower the melting temperature between DNA strands where the $c^7$dNTPs are incorporated allowing more efficient strand denaturation, and thus decreasing the number of compressions affecting the sequence data. One drawback with this method is the high cost of these modified molecules.

Another tactic used in an attempt to lower the melting temperature between DNA strands is the use of 2'-deoxyinosine-5'-triphosphate (dITP) in place of dGTP. However, dITP is not an ideal substrate for DNA polymerases and the results can be strong stops throughout the data, i.e., where one peak should appear from a fragment of specific size, three or more may be found co-migrating together. (See Barr P. J. et al., *Bio Techniques* 4(5):428–32, 1986.)

Needed in the art of DNA sequence analysis is an improved method that helps avoid DNA secondary structure artifacts during electrophoresis.

BRIEF SUMMARY OF THE INVENTION

In general, the present invention relates to nucleic acid sequencing methods. In particular, the present invention relates to the use of a mixture of 2' deoxynucleoside triphosphates for relief of sequencing gel compressions.

The present invention is an improved method of sequencing a DNA molecule comprising the step of exposing a template DNA molecule to a mixture of dITP and dGTP, or functional analogs, in the sequencing elongation reaction. By "DNA sequencing elongation reaction" we mean the elongation reaction occurring when a DNA template is exposed to a DNA polymerase, appropriate dNTPs, and specific chain terminators, such as ddNTPs. Preferably, the dI/dG mixture is between the molar ratios of 40:1 and 1:5. More preferably, the ratio is between 20:1 and 2:1. Most preferably, the ratio is 5:1.

In one embodiment of the present invention, the DNA polymerase used in the sequencing elongation reaction is a thermostable polymerase or a genetically engineered DNA polymerase. In another embodiment of the present invention, the polymerase is an N-terminal-deleted polymerase or a mutated version thereof. In a preferred form of the present invention, the polymerase has the amino acid sequence of *Thermus aquaticus* DNA polymerase excluding the N-terminal 280 amino acid residues or the F667Y mutation thereof. In another preferred form of the present invention, the polymerase is TAQUENASE, a commercially available modified sequencing enzyme (Δ280, F667Y Taq DNA polymerase), or T7 DNAP.

In one preferred form of the invention, the sequencing reaction is part of a cycle-sequencing protocol. In another preferred form of the invention, the sequencing reaction is part of an automated sequencing protocol. In another preferred form of the invention, the sequencing reaction is coupled to a polymerase chain reaction.

It is an object of the present invention to prevent compression artifacts generated in the gel during DNA electrophoresis.

Other objects, features and advantages of the present invention will become apparent after one has reviewed the specification, claims and drawings.

DETAILED DESCRIPTION OF THE INVENTION

The present invention discloses that a mixture of dGTP and dITP can release hairpin-like structures created during gel electrophoresis. (By "hairpin-like structures" we mean a formation that occurs when the last base or bases in a sequencing-generated fragment hybridize to one or several internal bases within the same fragment.) We postulate that by mixing dI and dG the introduction of dITP in the sequencing template will be randomized, thereby the negative effects of using only dITP will be minimized. As the DNAP enzyme is less efficient to introduce dITP than dGTP, a small amount of dGTP will be introduced even if there is an excess of dITP in the mixture, but some dITP will statistically be introduced. The presence of dITP will lower the denaturing temperature, and thereby, the hairpin structures will be easier to dissolve.

The present invention is a method for determining a nucleotide sequence for a template nucleic acid by chain termination sequence methods. Typically, the invention comprises the steps of first annealing an oligonucleotide primer to a template DNA molecule, and then adding deoxyadenine-5'-triphosphate (dATP); deoxythymine-5'-triphosphate (dTTP); a mixture of deoxyguanine-5'-triphosphate (dGTP) and deoxyinosine-5'-triphosphate (dITP), and deoxycytosine-5'-triphosphate (dCTP), or functional analogs thereof, chain terminators and a DNA polymerase, wherein a complementary strand synthesis reaction occurs. One then analyzes the results of the complementary strand synthesis reaction so that a nucleotide sequence of the template nucleic acid may be obtained.

By "functional analog" we mean analogs of any the dNTPs, such as $c^7$dATP and $c^7$dGTP, that substitute for the dNTPs typically used in the sequencing reaction and may be added for various reasons. For example, one might add alpha-thio-dNTPs in place of the standard dNTPs to resolve compressions.

By "chain terminators," we mean molecules that upon incorporation will stop nucleic acid chain elongation. A preferable chain terminator is a dideoxynucleotide.

Therefore, the present invention relates to a novel formulation of dNTP mixes for use in the elongation reaction during DNA sequencing. The present invention involves combining dITP and dGTP in sequencing mixes. The mixes help reduce gel artifacts known as compressions and allow unambiguous DNA sequence determination.

We envision that the method will be applicable to a number of DNA sequencing methods, such as cycle sequencing and standard DNA sequencing, both automated and manual.

Of particular significance to the present invention is automated DNA sequencing. The Examples below describe a preferred method of automated DNA sequencing according to the AutoRead Sequencing Kit (Pharmacia Biotech Inc.). The method of the present invention will be suitable for other automated sequencing reaction variations, however.

All methods of DNA sequencing suitable for the present invention have certain parameters in common. For example, when one prepares a DNA sequencing reaction, one prepares four different mixes with a specific chain terminator, preferably a ddNTP such as ddATP, ddCTP, ddGTP, or ddTTP, and various amounts of all four dNTPs. This provides a mix in which the specific ddNTP may substitute with a certain statistical frequency for one of the dNTPs. In the method of the present invention, one would substitute a particular molar ratio of dITP/dGTP of functional analogs thereof, for the dGTP typically found in the sequencing mixes.

A DNA template is exposed to one of the sequencing mixes and a DNA polymerase at buffer concentrations and pH appropriate for an elongation reaction to occur. Random incorporation of the dideoxynucleotide will provide a staggered selection of elongation products, each ending at a nucleotide corresponding to the added dideoxynucleotide. Size fractionation of all four sequencing reactions will provide a method of determining the sequence of the template molecule. Typically, this size fractionation is via electrophoresis, mass spectrometry or by the use of chromatographic methods. The sequence may be determined by reference to chromatograms (such as FIGS. 1–9) obtained from the size fractionated extension products by the use of electrophoresis. Each peak in these chromatograms represent the size of a DNA fragment terminated with one of the specific ddNTPs. The original template sequence is revealed by combining the terminated size fractionated DNA fragments from the four (A, C, G and T) different elongation/termination reactions (such as in FIGS. 1–9).

When using the method of the present invention, one will notice a lessening of the compression artifacts normally observed during electrophoresis. The Examples below demonstrate the magnitude of the subsequent corrected separation. In general, the formerly compressed nucleotides will now appear as normal, non-compressed nucleotides.

We have found, as disclosed in the Examples below, that molar ratios of dITP/dGTP of 40:1 to 1:5 are suitable for DNA polymerase in sequencing reactions. Preferably a ratio of 20:1 to 2:1 is used. Most preferably the ratio is 5:1. A different molar ratio of dITP to dGTP might be optimum for different DNA polymerases. The present invention might also affect DNAPs differently with respect to sequence reading length because of inherent enzyme variations in the capability to incorporate dITP.

Applicants envision that one would optimize the use and proper ratios of dITP and dGTP for other enzymes commonly used in DNA sequencing reactions, such as Klenow fragment, T7 DNAP, Taq DNAP, SEQUENASE (Amersham), and modified DNAPs. Preferably, thermostable polymerases such as *Thermus aquaticus* DNA polymerases (Taq) or other Taq-like polymerases would be useful. Particularly, end-terminal-deleted thermostable polymerases or mutated versions thereof, especially TAQ DNA polymerases excluding the end terminal 280 amino acid residues or the F667Y mutations, such as KLENTAQ 1 (AB Peptides, Inc., St. Louis, Mo.) and TAQUENASE (Wayne Barnes, Washington University, St. Louis, Mo.), are envisioned to be useful.

Each DNAP may require differing concentrations of both dNTPs and ddNTPs for optimization of either sequence reading lengths or signal intensities, or both. Concentrations of dNTPs may also be varied depending upon the methodology, e.g., mixes used with radiolabelled dNTPs would contain at least one dNTP at a substantially lower concentration than the other three for efficient label incorporation, while reactions for automated sequencing instruments may use higher concentrations of all dNTPs in the mixes to improve overall signal strength and read length.

One skilled in the art would recognize other variations or additions to the mixes that might be required for optimization of sequencing reactions using different DNAPs such as, but not limited to:

(a) Using a different buffer system, (b) Requiring a modified ddNTP (e.g., 3' amino-ddNTPs and T4 DNAP) for efficient fragment termination, (c) Addition other components (e.g., thermostable DNA binding proteins, ammonium sulfate, labelled dNTPs or ddNTPs, Triton X-100).

(d) Adding either $c^7dATP$ or $c^7dGTP$ or both together.

Optimization of dI/dG Mixes for DNA Polymerases

We envision that different DNA polymerases could have different optimization of the molar ratio of dI/dG. Therefore, one would optimize the dI/dG sequencing mixes for candidate DNA polymerases. One would typically examine an elongation reaction consisting of the candidate DNA polymerases and a DNA template and optimize several important parameters. These parameters would typically be:

(a) Change buffer (type and/or concentration) and pH.

(b) Add other components from the mixes, e.g., sodium chloride, $c^7dATP$, potassium chloride, ammonium sulphate.

(c) Vary the dITP:dGTP ratio.

One would choose the optimum pH and reaction conditions for the DNA polymerase in question and then vary the dI/dG ratios accordingly and observe length of read, compression relief and lack or appearance of strong stops. Preferably, both compression relief and read length are optimized.

EXAMPLES

The following examples disclose the use of several DNA templates (M13, t27, pCT41A, and pCYPAC) and both thermostable and non-thermostable DNA polymerases to demonstrate the efficacy of the present invention in various types of sequencing reactions.

A. Materials and Methods

The following enzymes were used for these examples:
(a) T7 DNA polymerase (Pharmacia Biotech Inc.),
(b) SEQUENASE Version 2.0 (Amersham),
(c) KLENTAQ 1, a 280 amino acid N-terminal deletion of the DNAP from *Thermus aquaticus*, as disclosed in Barnes U.S. Pat. No. 5,436,149,
(d) TAQUENASE, a 280 amino acid deletion containing a F667Y mutation in the polymerase domain as disclosed in Barnes, U.S. Pat. No. 5,436,149 and Tabor, European Patent Application 0 655 506 A1.

Sequencing of double-stranded DNA was according to the AutoRead Sequencing Kit instruction manual (Pharmacia Biotech Inc.). Briefly, 5 μg of template in a 10 μL volume of distilled water were denatured by the addition of 1.5 μL of 1N±0.005N sodium hydroxide (NaOH) and heating to 5 minutes at 65°–70° C. The denatured DNA was then placed at 37° C. where 1.5 μL of 1N±0.005N HCl, 2 μL of AutoRead Kit Annealing Buffer, and 4–6 picomoles of sequencing primer containing a labelled 5' end were added. After a further 10 minute incubation at 37° C., the above mixture was allowed to cool at room temperature for 5–10 minutes. Once cool, 2 μL of T7 DNAP at a concentration of between 6–8 units/μL, 1 μL of AutoRead Sequencing Kit Extension Buffer, and 3.5 μL of dimethyl sulfoxide were added. 5.4 μL of the mixture were then immediately added to the AutoRead Sequencing Kit Sequencing Mixes (A, C, G, and T) which had been prewarmed at 37° C. Each reaction was allowed to continue at 37° C. for 5 minutes when 6 μL of AutoRead Sequencing Kit Stop Solution were added. The reactions were kept cold until heat denatured and loaded on an automated DNA sequencing instrument.

Sequencing of single-stranded DNA was according to the AutoRead Sequencing Kit instruction manual (Pharmacia Biotech Inc.). Briefly, a 17 μL mix was prepared containing 2 μg of template, distilled water, 2 μL of AutoRead Kit Annealing Buffer, and 2–4 picomoles of sequencing primer with a labelled 5' end. The mixture was heated at 65°–70° C. for 10 minutes and then cooled at room temperature for 10 minutes. 2 μL of T7 DNAP at a concentration of between 2–4 units/μL and 1 μL of AutoRead Sequencing Kit Extension Buffer were added and 4.5 μL of the mixture immediately aliquoted to 2.5 μL of each AutoRead Sequencing Kit Sequencing Mix (A, C, G, & T) which had been prewarmed at 37° C. The reactions were allowed to continue at 37° C. for 5 minutes when 6 μL of AutoRead Sequencing Kit Stop Solution were added. The reactions were kept cold until heat denatured and loaded on an automated DNA sequencing instrument.

Sequencing mixes used in Sanger-type sequence analysis contain different substances depending upon which DNAP is used to generate the DNA fragments. Table 1, below, discloses exemplary sequencing mixes used with both TAQUENASE DNA polymerase and T7 DNA Polymerase. T7 Sequencing Mixes (see Table 1, below) typically contain Tris-HCl, four dNTPs (A, C, G, and T), NaCl, and a specific ddNTP. Some thermostable DNAPs, such as Taq or TAQUENASE (see Table 1), omit the NaCl from the mixes due to its inhibitory effect upon the enzyme.

Cycle sequencing of double-stranded DNA was according to the AutoCycle Sequencing Kit instruction manual (Pharmacia Biotech Inc.) for Taq and Klentaq 1 DNAPs. A modification of the Sequencing Mixes, as outlined in Table 1 and below, was required for TAQUENASE. Briefly, an 18 μL master mix was prepared containing 250 ng-1 μg template DNA, buffer, 1–2 pmoles of labelled primer, 2.5 units of DNAP, 5 μL of dNTP Solution and 8% dimethyl sulfoxide. 4 μL of the Master Mix were then distributed to 2 μL of each ddNTP solution, covered with mineral oil, and subjected to the following thermal cycling program:
(a) A hot start at 95° C. for two minutes,
(b) 25–30 cycles of incubation at the following temperatures for the indicated times: 95° C. for 36 seconds, followed by 50° C. for 36 seconds, and then 72° C. for 84 seconds,
(c) One cycle holding the temperature at 4° C. until electrophoresis.

TABLE 1

| Component | A Mix | C Mix | G Mix | T Mix |
|---|---|---|---|---|
| Taquenase DNA polymerase (5:1 dI:dG ratio) | | | | |
| Specific ddNTP | 5 μM | 5 μM | 2.75 μM | 5 μM |
| dATP | 1 mM | 1 mM | 1 mM | 1 mM |
| dCTP | 1 mM | 1 mM | 1 mM | 1 mM |
| dGTP | 0.4 mM | 0.4 mM | 0.4 mM | 0.4 mM |
| dTTP | 1 mM | 1 mM | 1 mM | 1 mM |
| dITP | 1.6 mM | 1.6 mM | 1.6 mM | 1.6 mM |
| Tris-HCl, pH 9.5 | 50 mM | 50 mM | 50 mM | 50 mM |
| T7 DNA Polymerase (5:1 dI:dG ratio) | | | | |
| Specific ddNTP | 5 μM | 5 μM | 5 μM | 5 μM |
| dATP | 1 mM | 1 mM | 1 mM | 1 mM |
| dCTP | 1 mM | 1 mM | 1 mM | 1 mM |
| dGTP | 0.4 mM | 0.4 mM | 0.4 mM | 0.4 mM |
| dTTP | 1 mM | 1 mM | 1 mM | 1 mM |
| dITP | 1.6 mM | 1.6 mM | 1.6 mM | 1.6 mM |
| Tris-HCl, pH 9.5 | 50 mM | 50 mM | 50 mM | 50 mM |
| NaCl | 40 mM | 40 mM | 40 mM | 40 mM |

The following templates were used for DNA Sequencing: t27 and pCT41A (templates chosen because of their known compression artifacts), M13 DNA, and plasmid pCYPAC. Templates t27 and pCT41A are described below. M13 DNA is commonly available from many sources. Plasmid PCYPAC is a 130 kb-construct.

B. Results

To demonstrate compression relief using this invention, two different templates containing three different known compression artifacts were subcloned using standard molecular biology techniques into double-stranded plasmid vector (pT7T3 18U; Pharmacia Biotech Inc.). Each template was then sequenced with either T7 DNAP or a thermostable DNAP using modified sequencing mixes as described above for double-stranded templates.

(a) t27 is approximately a 400 base insert of the human thymidine gene. (References for the original material are Flemington, E., et al., *Gene* 52:267–277, 1987 and Arcot, S. S., et al., *J. Biol. Chem.* 264;2343–2349, 1989.) The compression is 5'-GAG CCA TAG-3' (SEQ ID NO:1), about 100 bases into the sequence using the M13 universal primer (Pharmacia Biotech Inc.), and obscured sequence data from the automated sequencing instrument is demonstrated by the chromatogram in FIG. 1 (arrow).

Figure 1:
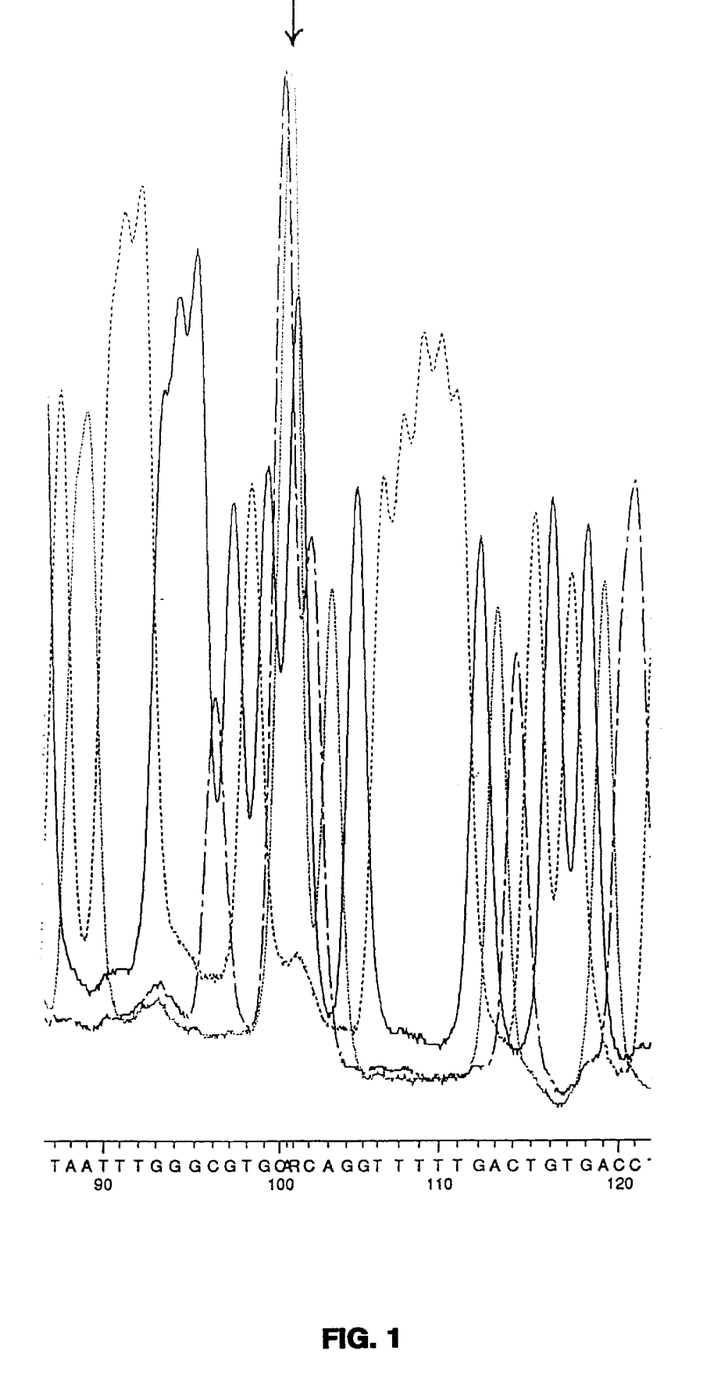
FIG. 1 is a chromatogram of nucleotides 87–121 of an automated sequencing reaction using t27 as the template with sequencing mixes containing dGTP with no dITP. The arrow denotes the compressed region.
Figure 2:
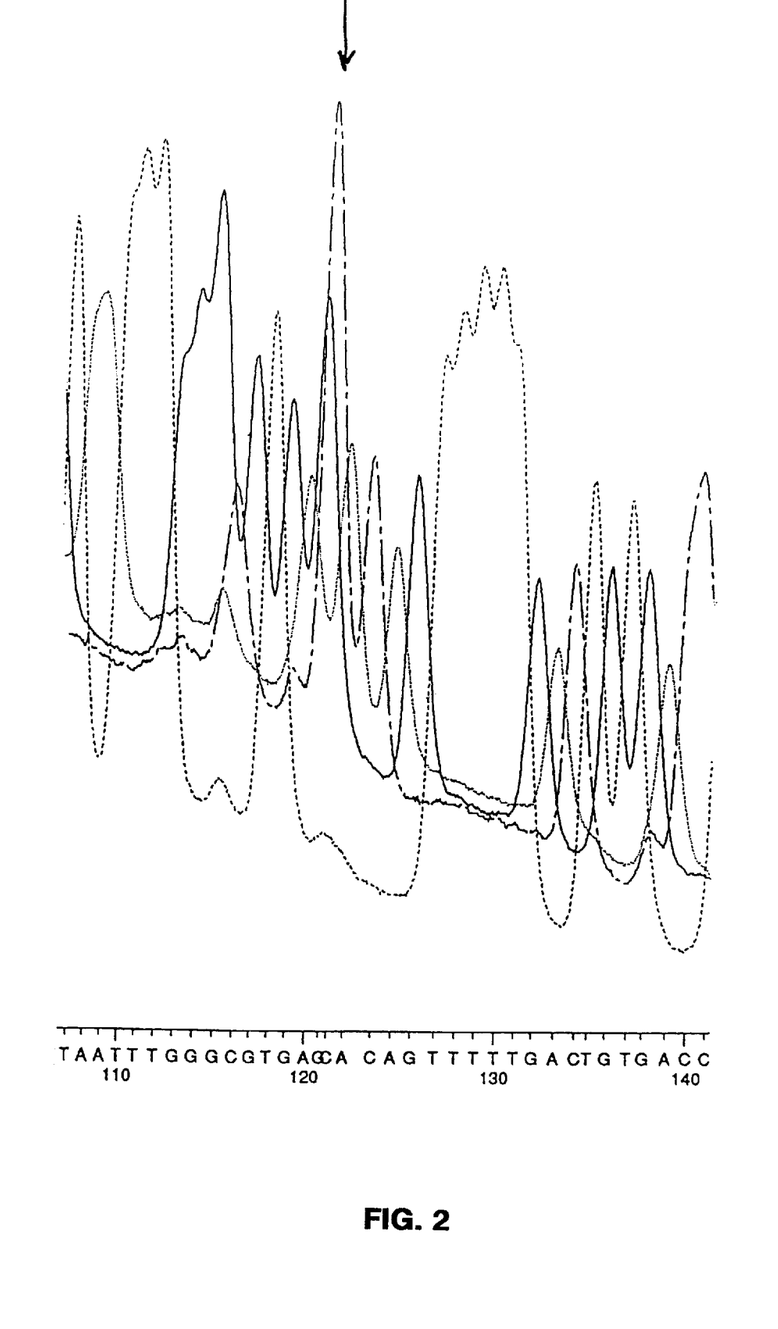
FIG. 2 is a chromatogram of nucleotides 87–121 of an automated sequencing reaction using t27 as the template with sequencing mixes containing $c^7$dGTP. The arrow denotes the compressed region.
Figure 3:
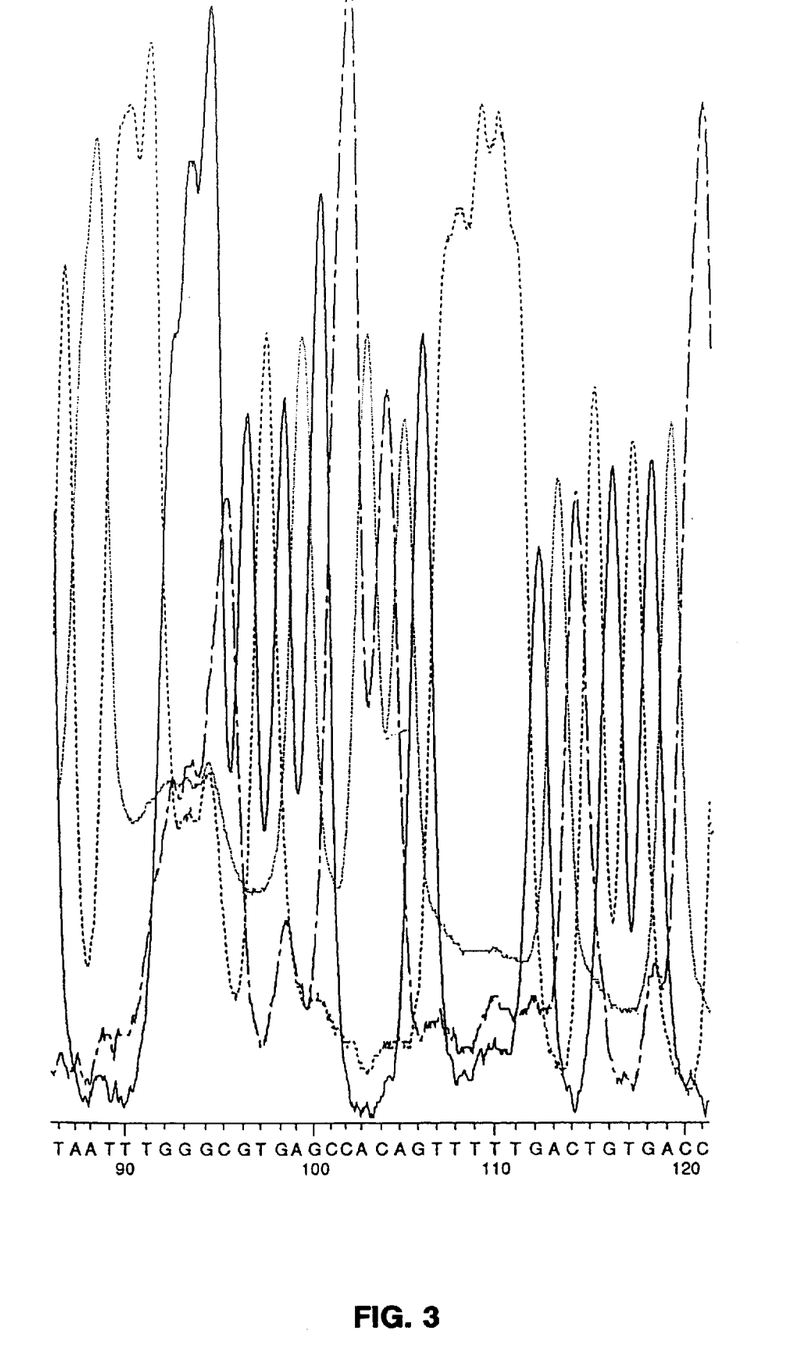
FIG. 3 is a chromatogram of nucleotides 87–121 of an automated sequencing reaction using t27 as the template with sequencing mixes containing both $c^7$dGTP and $c^7$dATP.
Figure 4:
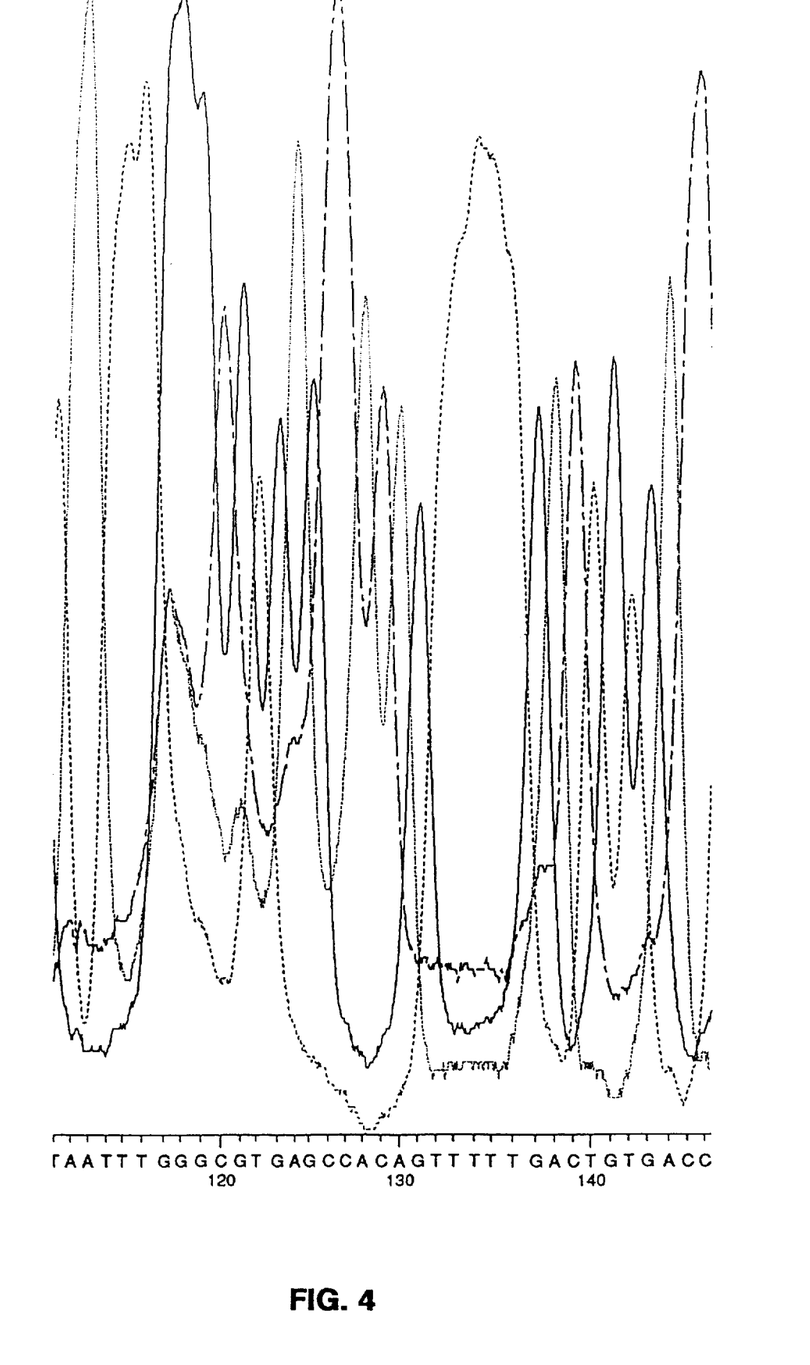
FIG. 4 is a chromatogram of nucleotides 87–121 of an automated sequencing reaction using t27 as the template with sequencing mixes containing both dITP and dGTP at a 5:1 molar ratio.

FIGS. 1–4 are chromatograms generated during automated sequencing reactions of nucleotides 87–121 of template t27. FIG. 1 is a chromatogram of a sequencing reaction with sequencing mixes containing dGTP with no dITP. The arrow denotes the compressed region. FIG. 2 is a chromatogram of a sequencing reaction with sequencing mixes containing $c^7$dGTP. The arrow denotes the compressed region. FIG. 3 is a chromatogram of a sequencing reaction with sequencing mixes containing both $c^7$dGTP and $c^7$dATP. FIG. 4 is a chromatogram of a sequencing reaction with sequencing mixes containing both dITP and dGTP at a 5:1 molar ratio.

FIGS. 2, 3, and 4 demonstrate compression relief using either c⁷dGTP, a combination of c⁷dATP and c⁷dGTP, or a 5:1 molar ratio of dITP to dGTP, respectively, in the sequencing mixes. While resolution of the compression improves when c⁷dGTP is used, the best sequence data is seen using either the expensive mixture of c⁷dATP and c⁷dGTP or this invention.

(b) pCT41A is a 41 base synthetic oligonucleotide containing two compression sites cloned into PT7T3 181. (Reference for the original material is Tabor, S. and C. C. Richardson, *Proc. Natl. Acad. Sci USA* 84:4767–4771, 1987.)

Figure 5:
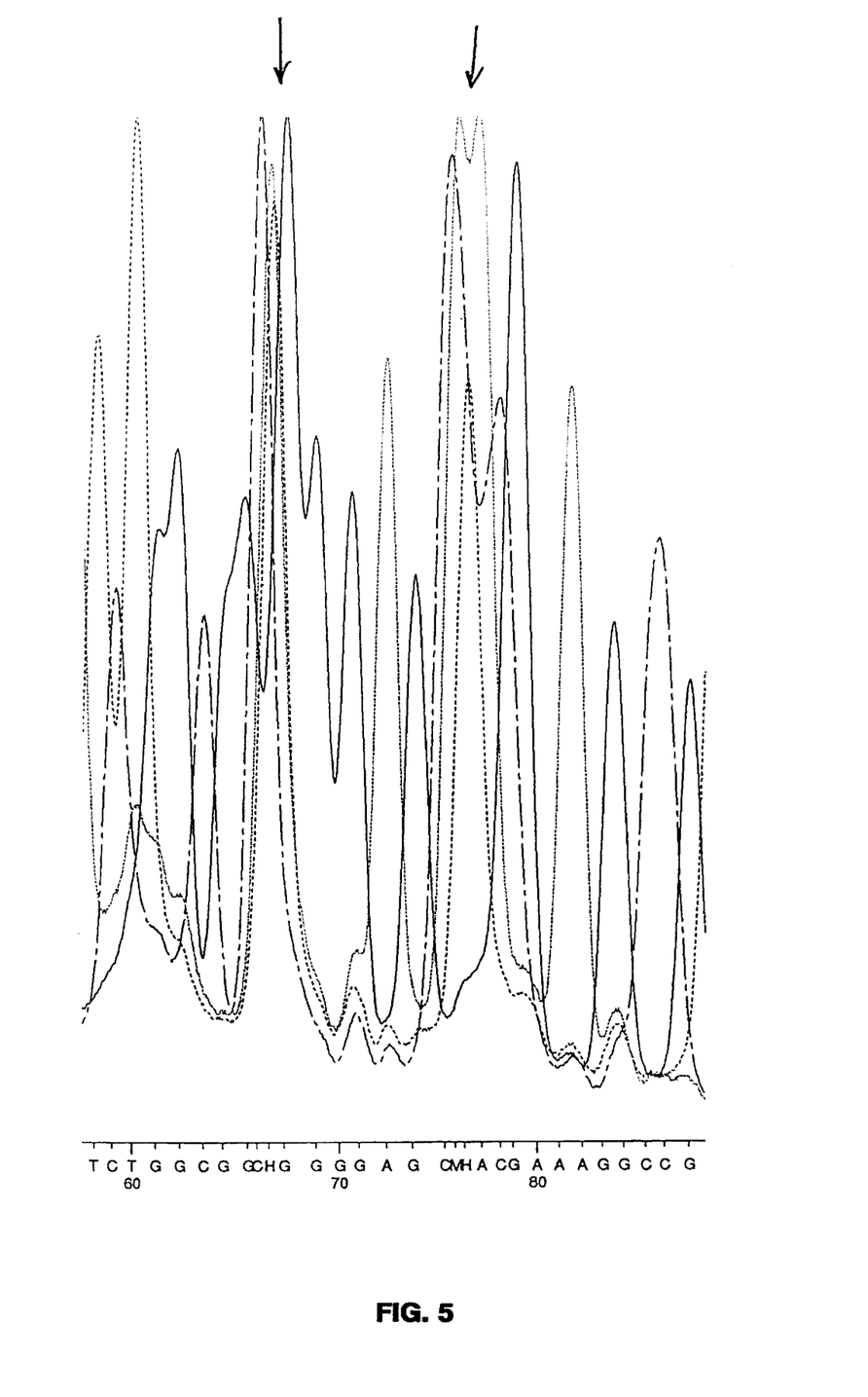
FIG. 5 is a chromatogram of nucleotides 58–87 of an automated sequencing reaction using pCT41A as the template with sequencing mixes containg dGTP. The arrows denote the compressed regions.
Figure 6:
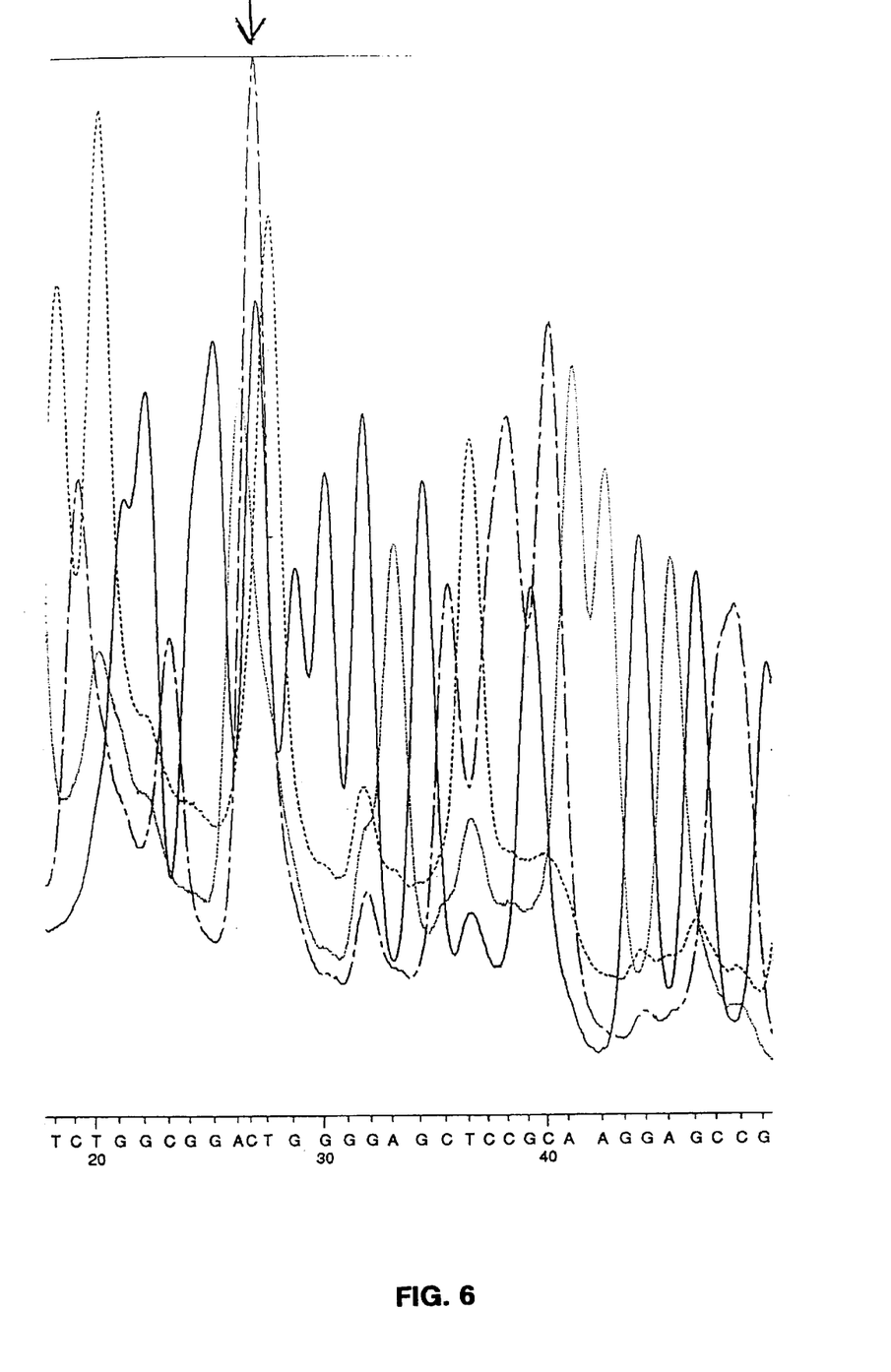
FIG. 6 is a chromatogram of the same DNA sequence as in FIG. 5 of an automated sequencing reaction using pCT41A as the template with sequencing mixes containing $c^7$dGTP. The arrow denotes the compressed region.
Figure 7:
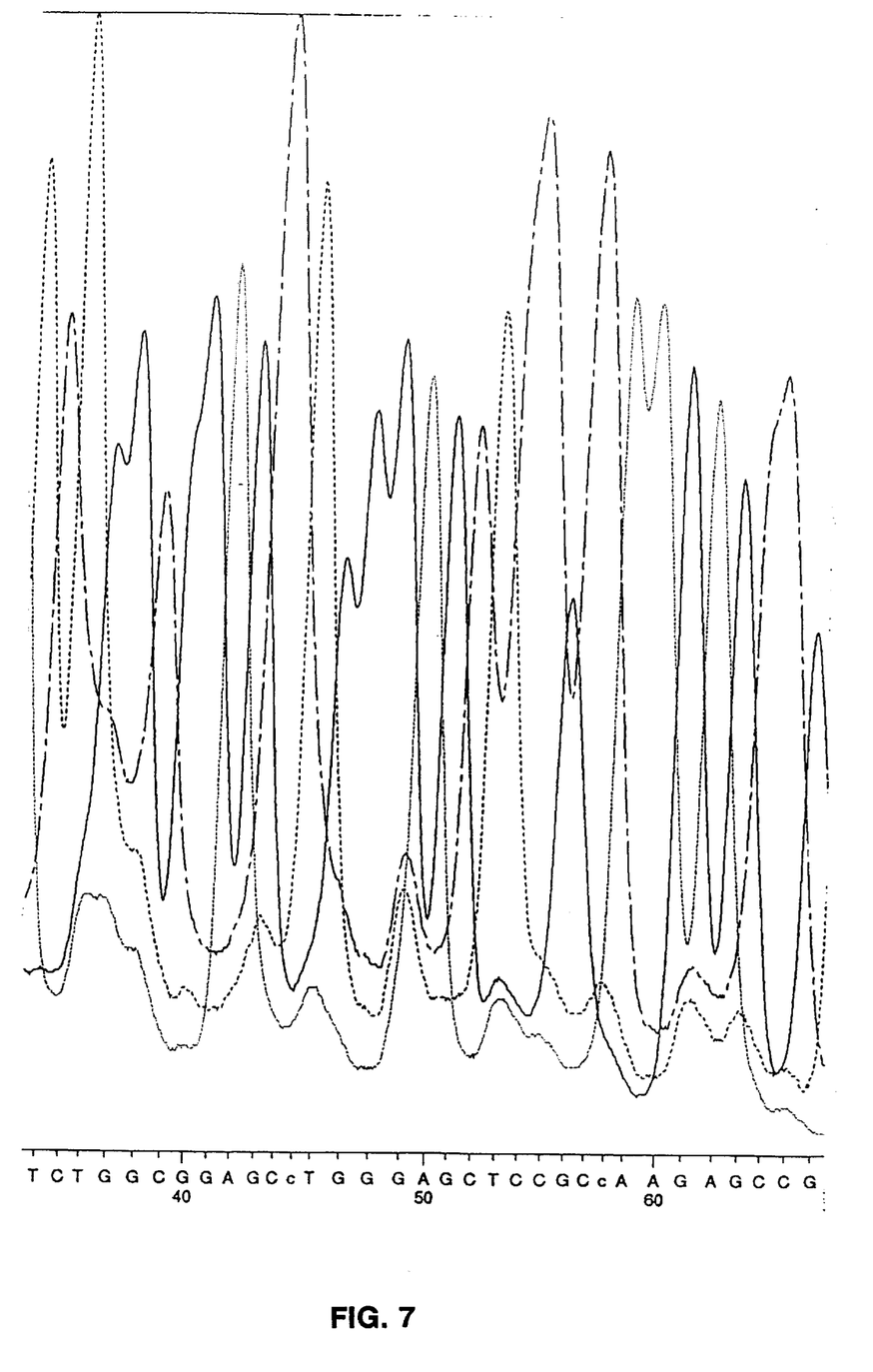
FIG. 7 is a chromatogram of the same DNA sequence as in FIG. 5 of an automated sequencing reaction using pCT41A as the template with sequencing mixes containing both $c^7$dGTP AND $c^7$dATP.
Figure 8:
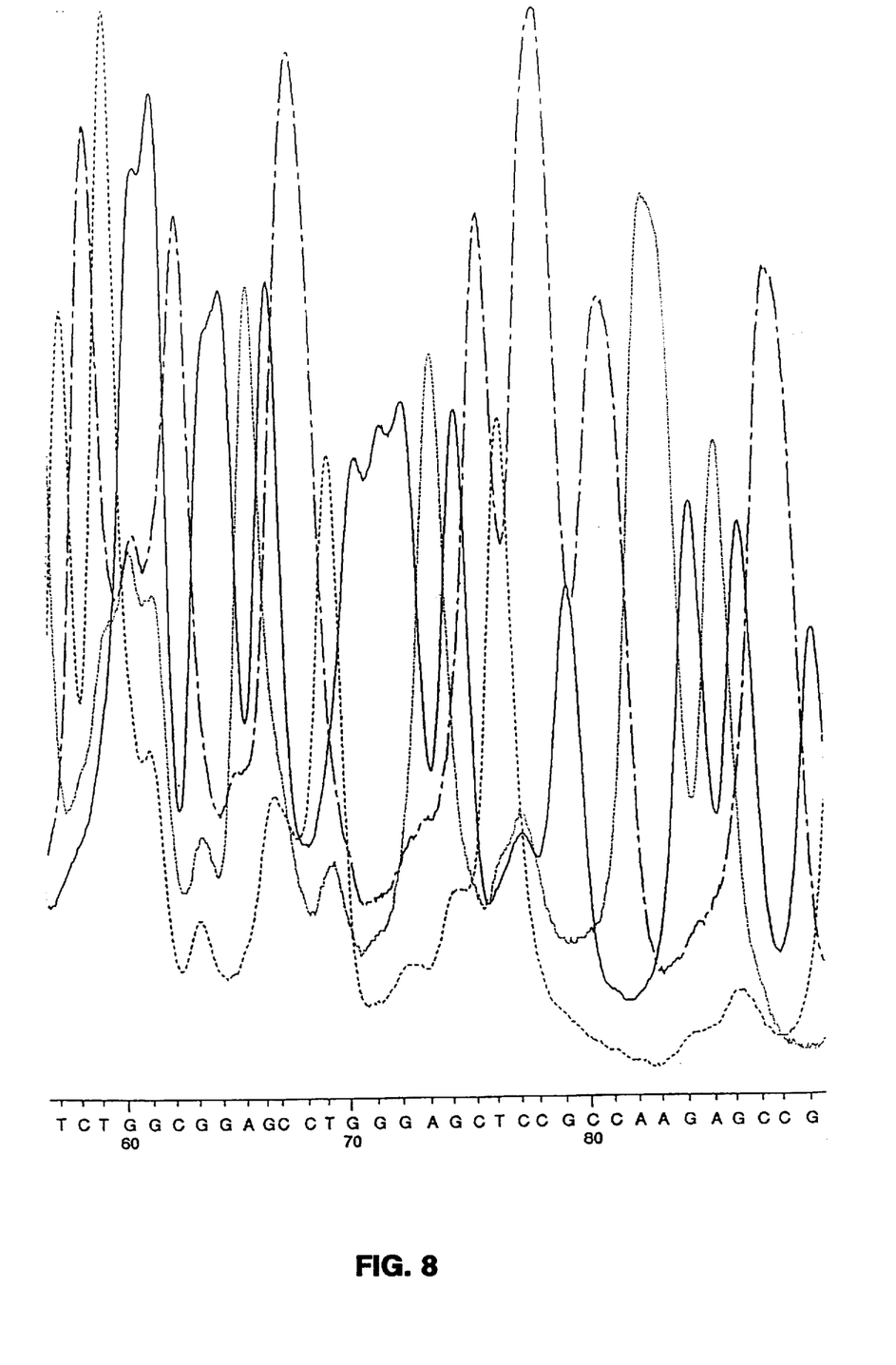
FIG. 8 is a chromatogram of the same DNA sequence as in FIG. 5 of an automated sequencing recation using pCT41A as the template with sequencing mixes containing dITP and dGTP in a 5:1 molar ratio.

FIGS. 5–8 are chromatograms of nucleotides 58–87 of an automated sequencing reaction using pCT41A as the template. FIG. 5 is a chromatogram of a sequencing reaction with sequencing mixes containg dGTP. The arrows denote the compressed regions. FIG. 6 is a chromatogram of a sequencing reaction with sequencing mixes containing c⁷dGTP. The arrow denotes the compressed region. FIG. 7 is a chromatogram of a sequencing reaction with sequencing mixes containing both c⁷dGTP and c⁷dATP. FIG. 8 is a chromatogram of a sequencing reaction with sequencing mixes containing dITP and dGTP in a 5:1 molar ratio.

One of the compressions, approximately 65 bases into the sequence using the M13 universal primer, is resolved with c⁷dATP as demonstrated in FIGS. 5 and 7. The second compression, approximately 75 bases into the sequence using the M13 universal primer, is resolved with c⁷dGTP as demonstrated in FIG. 6. Surprisingly, the readability of the sequence is enhanced further with the resolution of both compressions, as demonstrated in FIG. 8.

Figure 9A:
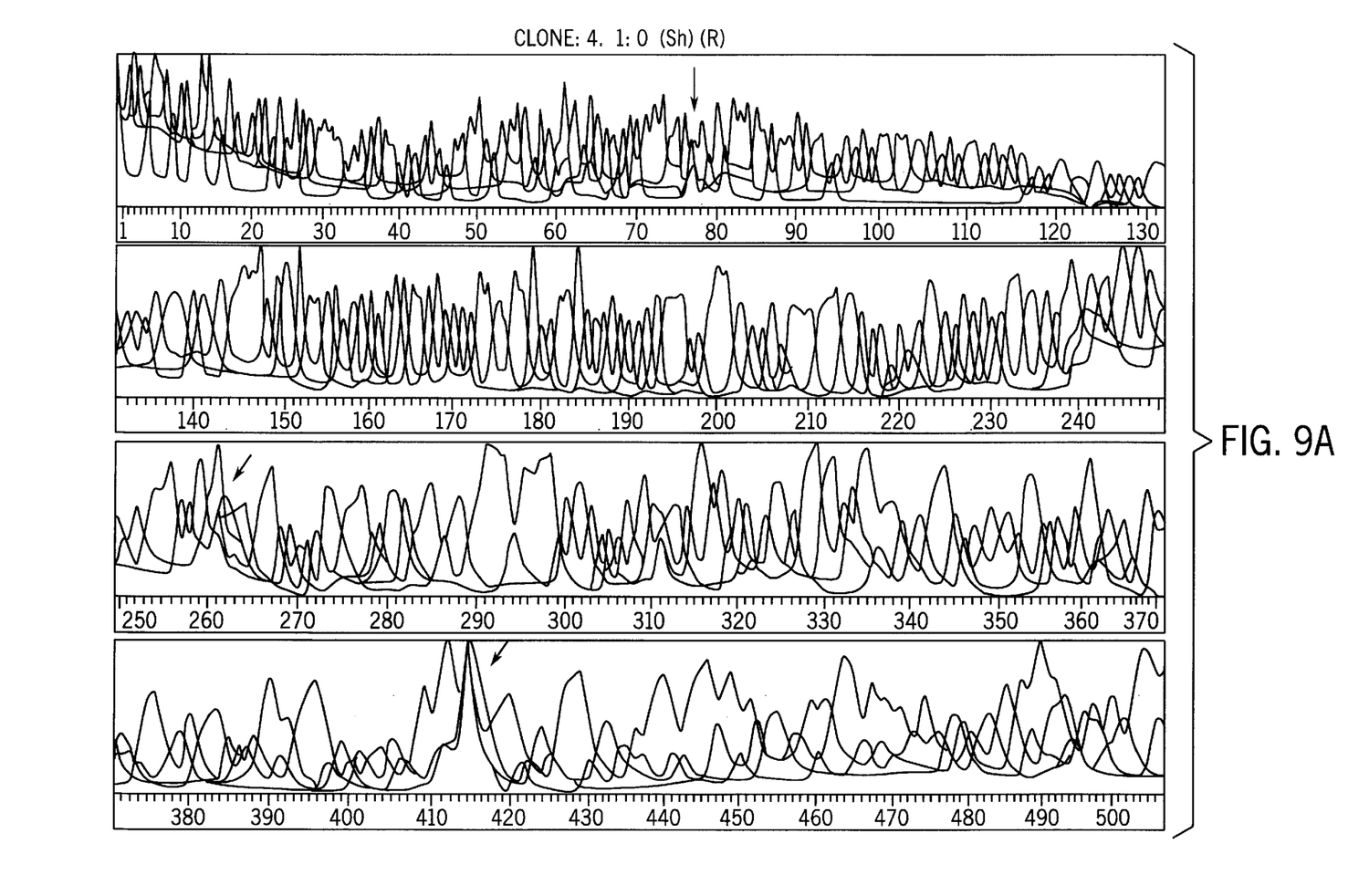
FIGS. 9A, B and C is a chromatogram of an automated sequencing reaction using M13 DNA as a template with sequencing reactions containing dITP (FIG. 9A), a 1:5 molar ratio of dITP:dGTP (FIG. 9B) and a 5:1 molar ratio of dITP:dGTP (FIG. 9C)
Figure 9B:
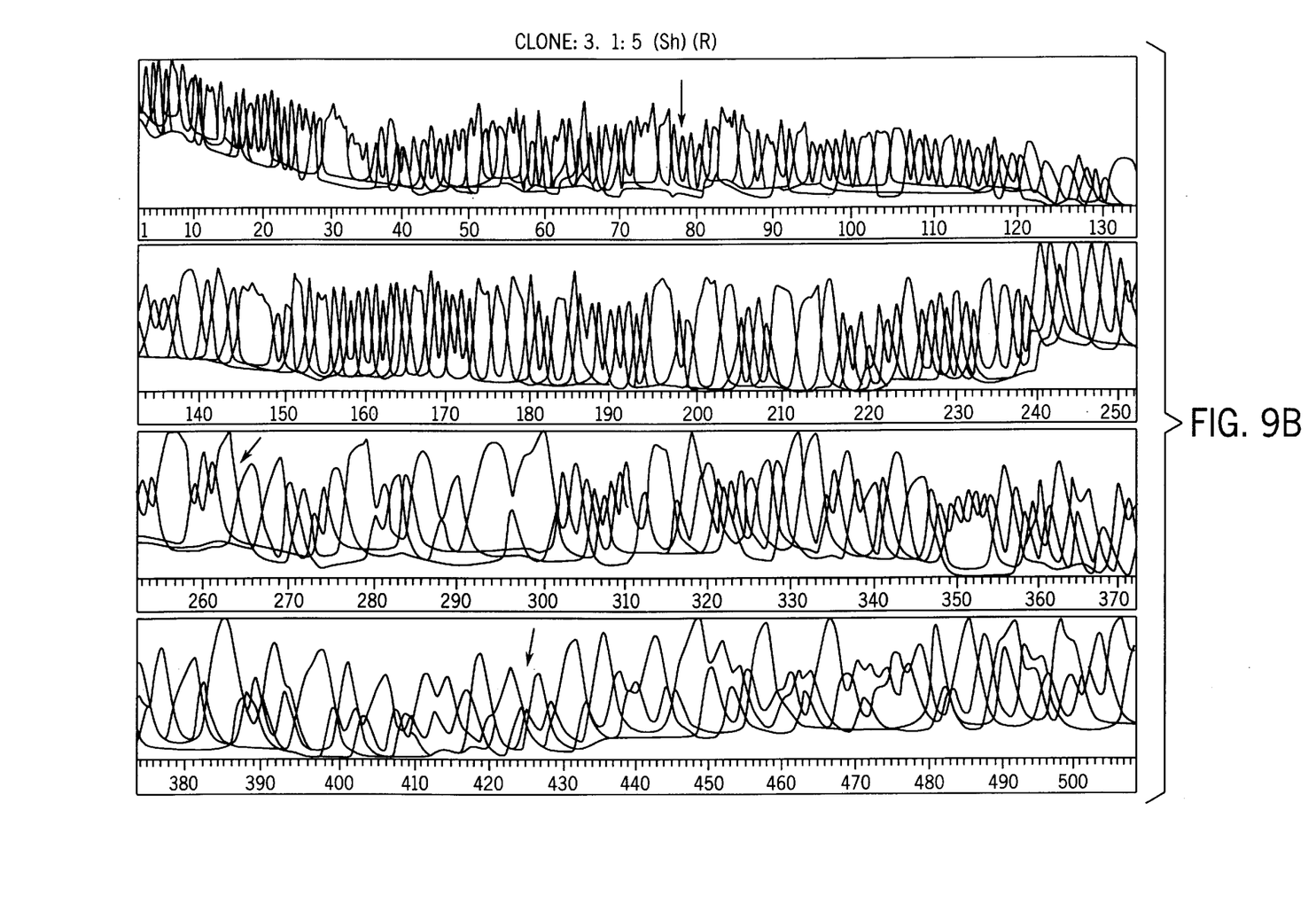
Figure 9C:
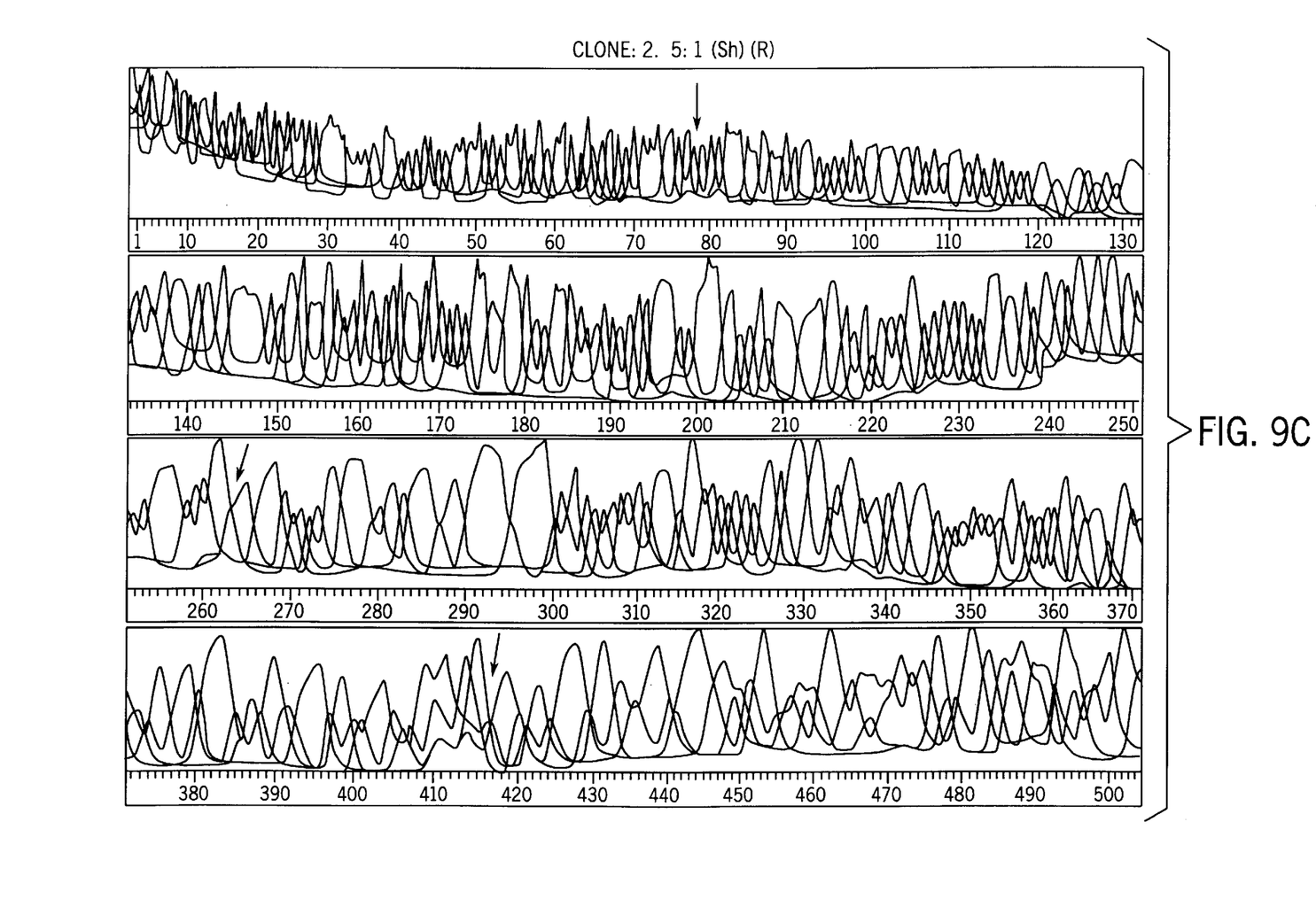

The dITP/dGTP sequencing mixes were tested using T7 DNA polymerase with an M13 template (see FIG. 9A). FIGS. 9A, B and C is a chromatogram of an automated sequencing reaction using M13 DNA as a template with sequencing reactions containing dITP (FIG. 9A), a molar ratio of 1:5 dITP to dGTP (FIG. 9B) and a 5:1 molar ratio of dITP to dGTP (FIG. 9C).

The set of components examined in FIG. 9A would not give extended read lengths (e.g., greater than 800 bases) using an automated DNA sequencing instrument while continuing to resolve compression artifacts. FIG. 9A demonstrates the inherent problems associated with T7 sequencing mixes substituting dITP for dGTP directly using the single-stranded template M13mp18(+) strand; note the stops at approximately 78, 260 and 410 bases into the sequence. FIG. 9B is the same template using a molar ratio of 1:5 dITP to dGTP in the sequencing mixes; note that the stops seen in FIG. 9A are no longer present. The mixes disclosed in Table 1, demonstrated in FIG. 9C, also function to prevent the strong stops seen in FIG. 9A.

Surprisingly, when the mix formulation from Table 1, above, was used with a thermostable DNAP, TAQUENASE, in a cycle sequencing reaction on pCYPAC template, sequencing read lengths of greater than 1000 bases were achieved without compression artifacts.

---

We claim:

1. A method for determining a nucleotide sequence for a template nucleic acid by a chain termination sequence method comprising the steps of
   a) annealing an oligonucleotide primer to a template DNA molecule,
   b) adding deoxyadenine-5'-triphosphate (dATP; deoxythymine-5'-triphosphate (dTTP); a mixture of deoxyguanine-5'-triphosphate (dGTP) and deoxyinosine-5'-triphosphate (dITP), and deoxycytosine-5'-triphosphate (dCTP), or functional analogs thereof, and chain terminators, and a DNA polymerase, wherein a complementary strand synthesis reaction occurs; and
   c) analyzing the results of the complementary strand synthesis reaction so that a nucleotide sequence of the template nucleic acid may be obtained.

2. The method of claim 1, wherein the ratio of dITP:dGTP is between 40:1 and 1:5.

3. The method of claim 2, wherein the ratio of dITP:dGTP is between 20:1 and 2:1.

4. The method of claim 1, wherein the ratio of dITP:dGTP is 5:1.

5. The method of claim 1, wherein the mixture of dITP and dGTP comprises a mixture of $c^7$dGTP and dITP.

6. The method of claim 1, wherein the polymerase is a thermostable DNA polymerase.

7. The method of claim 4, wherein the polymerase is an N-terminal deleted DNA polymerase.

8. The method according to claim 7, wherein the polymerase is selected from the group consisting of a polymerase having an amino acid sequence as that of *Thermus aquaticus* DNA polymerase excluding the N-terminal 280 amino acid residues and the F667Y mutation thereof.

9. The method of claim 1 wherein the polymerase is T7 DNA polymerase.

10. The method of claim 1, wherein the sequencing method is according to a cycle sequencing protocol.

11. The method of claim 1, wherein the sequencing method is according to an automated sequencing protocol.

12. The method of claim 1, wherein the template nucleic acid sequence is amplified by polymerase chain reaction.

\* \* \* \* \*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

GAGCCATAG        9

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

TAATTTGGGC GTGCARCAGG TTTTTGACTG TGACC        35

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single (D) TOPOLOGY: linear (i i) MOLECULE TYPE: DNA (genomic)

(x i) SEQUENCE DESCRIPTION: SEQ ID NO:3:

TAATTTGGGC GTGAGCACAG TTTTTGACTG TGACC 35

(2) INFORMATION FOR SEQ ID NO:4:

(i) SEQUENCE CHARACTERISTICS:
  (A) LENGTH: 36 base pairs
  (B) TYPE: nucleic acid
  (C) STRANDEDNESS: single
  (D) TOPOLOGY: linear  (i i) MOLECULE TYPE: DNA (genomic)

(x i) SEQUENCE DESCRIPTION: SEQ ID NO:4:

TAATTTGGGC GTGAGCCACA GTTTTTGACT GTGACC 36

(2) INFORMATION FOR SEQ ID NO:5:

(i) SEQUENCE CHARACTERISTICS:
  (A) LENGTH: 33 base pairs
  (B) TYPE: nucleic acid
  (C) STRANDEDNESS: single
  (D) TOPOLOGY: linear  (i i) MOLECULE TYPE: DNA (genomic)

(x i) SEQUENCE DESCRIPTION: SEQ ID NO:5:

TCTGGCGGAG CCTGGGAGCT CCGCCAAGAG CCG 33

(2) INFORMATION FOR SEQ ID NO:6:

(i) SEQUENCE CHARACTERISTICS:
  (A) LENGTH: 30 base pairs
  (B) TYPE: nucleic acid
  (C) STRANDEDNESS: single
  (D) TOPOLOGY: linear  (i i) MOLECULE TYPE: DNA (genomic)

(x i) SEQUENCE DESCRIPTION: SEQ ID NO:6:

TCTGGCGGCH GGGGAGCMHA CGAAAGGCCG 30

(2) INFORMATION FOR SEQ ID NO:7:

(i) SEQUENCE CHARACTERISTICS:
  (A) LENGTH: 32 base pairs
  (B) TYPE: nucleic acid
  (C) STRANDEDNESS: single
  (D) TOPOLOGY: linear  (i i) MOLECULE TYPE: DNA (genomic)

(x i) SEQUENCE DESCRIPTION: SEQ ID NO:7:

TCTGGCGGAC TGGGGAGCTC CGCAAGGAGC CG 32

(2) INFORMATION FOR SEQ ID NO:8:

(i) SEQUENCE CHARACTERISTICS:
  (A) LENGTH: 33 base pairs
  (B) TYPE: nucleic acid
  (C) STRANDEDNESS: single
  (D) TOPOLOGY: linear  (i i) MOLECULE TYPE: DNA (genomic)

(x i) SEQUENCE DESCRIPTION: SEQ ID NO:8:

TCTGGCGGAG CCTGGGAGCT CCGCCAAGAG CCG                                          33

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:9:

TCTGGCGGAG CCTGGGAGCT CCGCCAAGAG CCG                                          33

(2) INFORMATION FOR SEQ ID NO:10:

(i) SEQUENCE CHARACTERISTICS:
        (A) LENGTH: 506 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:10:

GCATGCCTGC AGGTCGACTC TAGAGGATCC CCGGGTACCG AGCTCGAATT CGTAATCATG             60
GTCATAGCTG TTTCCTGTGT GAAATTGTTA TCCGCTCACA ATTCCACACA ACATACGAGC            120
CGGAAGCATA AAGTGTAAAG CCTGGGGTGC CTAATGAGTG AGCTAACTCA CATTAATTGC            180
GTTGCGCTCA CTGCCCGCTT TCCAGTCGGG AAACCTGTCG TGCCAGCTGC ATTAATGAAT            240
CGGCCAACGC GCGGGGAGAG GCGGTTTGCG TATTGGGCGC CAGGGTGGTT TTTCTTTTCA            300
CCAGTGAGAC GGGCAACAGC TGATTGCCCT TCACCGCCTG GCCCTGAGAG AGTTGCAGCA            360
AGCGGTSCCA CGCTGGTTTG CCCCAGCAGG CGAAAATCCT GTTTGATGGT KGTTYCGMAA            420
TCGGCAAAAT CCCTTATAAA TCAAAGAAT AGCCCGAGAT AGGGGTGAGT GTTGTTCCAG             480
TTTGGAACAA GAGTCCACTA TTAAAG                                                 506

(2) INFORMATION FOR SEQ ID NO:11:

(i) SEQUENCE CHARACTERISTICS:
        (A) LENGTH: 505 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:11:

GCATGCCTGC AGGTCGACTC TAGAGGATCC CCGGGTACCG AGCTCGAATT CGTAATCATG             60
GTCATAGCTG TTTCCTGTGT GAAATTGTTA TCCGCTCACA ATTCCACACA ACATACGAGC            120
CGGAAGCATA AAGTGTAAAG CCTGGGGTGC CTAATGAGTG AGCTAACTCA CATTAATTGC            180
GTTGCGCTCA CTGCCCGCTT TCCAGTCGGG AAACCTGTCG TGCCAGCTGC ATTAATGAAT            240
CGGCCAACGC GCGGGGAGAG GCGGTTTGCG TATTGGGCGC CAGGGTGGTT TTTCTTTTCA            300
CCAGTGAGAC GGGCAACAGC TGATTGCCCT TCACCGCCTG GCCCTGAGAG AGTTGCAGCA            360
AGCGGTGCAC GCTGGTTTGC CCCAGCAGGC GAAAATCCTG TTTGATGGTG TTCCGAAAT             420
CGGCAAAATC CCTTATAAAT CAAAGAATA GCCCGAGATA GGGTTGAGTG TTGTTCCAGT             480
TTGGAACAAG AGTCCACTAT TAAAG                                                  505

(2) INFORMATION FOR SEQ ID NO:12:

(i) SEQUENCE CHARACTERISTICS:
        (A) LENGTH: 504 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:12:

```
GCATGCCTGC  AGGTCGACTC  TAGAGGATCC  CCGGGTACCG  AGCTCGAATT  CGTAATCATG     60
GTCATAGCTG  TTTCCTGTGT  GAAATTGTTA  TCCGCTCACA  ATTCCACACA  ACATACGAGC    120
CGGAAGCATA  AAGGTGTAAA  GCCTGGGGTG  CCTAATGAGT  GAGCTAACTC  ACATTAATTG    180
CGTTGCGCTC  ACTGCCCGCT  TTCCAGTCGG  GAAACCTGTC  GTGCCAGCTG  CATTAATGAA    240
TCGGCCAACG  CGCGGGGAGA  GGCGGTTTGC  GTATTGGGCG  CCAGGGTGGT  TTTTCTTTTC    300
ACCAGTGAGA  CGGGCAACAG  CTGATTGCCC  TTCACCGCCT  GGCCCTGAGA  GAGTTGCAGC    360
AAGCGGTCCA  CGCTGGTTTG  CCCCAGCAGG  CGAAAATCCT  GTTTGATGGT  GGTYCGAAAT    420
CGGCAAAATC  CSTTATAAAT  CAAAAGAATA  GCCCGAGATA  GGGTTGAGTG  TTGTTCCAGT    480
TTGGAACAAG  AGTCACTATT  AAAG                                              504
```